United States Patent [19]
Gaborski et al.

[11] Patent Number: 5,661,818
[45] Date of Patent: Aug. 26, 1997

[54] METHOD AND SYSTEM FOR DETECTING GRIDS IN A DIGITAL IMAGE

[75] Inventors: Roger S. Gaborski, Pittsford; Thaddeus F. Pawlicki, Akron, both of N.Y.

[73] Assignee: Eastman Kodak Company, Rochester, N.Y.

[21] Appl. No.: 379,389

[22] Filed: Jan. 27, 1995

[51] Int. Cl.$^6$ .................................................. G06K 9/00
[52] U.S. Cl. ............................................. 382/132; 378/164
[58] Field of Search ..................................... 382/132, 199, 382/202, 263, 287; 378/86, 87, 163, 164

[56] References Cited

U.S. PATENT DOCUMENTS

| | | | |
|---|---|---|---|
| 4,468,697 | 8/1984 | Verhoeven | 358/111 |
| 4,870,692 | 9/1989 | Zuiderveld et al. | 382/6 |
| 4,875,227 | 10/1989 | Rossi et al. | 378/154 |
| 4,918,713 | 4/1990 | Honda | 378/99 |
| 4,939,760 | 7/1990 | Kawai | 378/99 |
| 5,050,198 | 9/1991 | Honda | 378/99 |
| 5,101,448 | 3/1992 | Kawachiya et al. | 382/61 |
| 5,202,552 | 4/1993 | Little et al. | 235/494 |
| 5,204,919 | 4/1993 | Murakami | 382/54 |
| 5,224,177 | 6/1993 | Doi et al. | 382/54 |
| 5,231,574 | 7/1993 | Agano | 364/413.13 |
| 5,294,989 | 3/1994 | Moore et al. | 348/241 |
| 5,357,554 | 10/1994 | Schneiderman et al. | 378/155 |

FOREIGN PATENT DOCUMENTS

| | | | |
|---|---|---|---|
| 5-40847 | 2/1993 | Japan | 382/202 |

*Primary Examiner*—Andrew Johns
*Attorney, Agent, or Firm*—Peyton C. Watkins

[57] ABSTRACT

A method for detecting grids in a digital image having a plurality of pixels for capturing an image, comprises the steps of performing a high pass filter operation on a sample of pixels for filtering out the image from the sampled pixels; and performing a statistical F-test operation on the results of the high pass filter operation for determining when the digital image contains grids.

18 Claims, 3 Drawing Sheets

METHOD AND SYSTEM FOR DETECTING GRIDS IN A DIGITAL IMAGE

BACKGROUND OF THE INVENTION

1. Field of Invention

The invention relates generally to a method and system for detecting grids in a digital image.

2. Background of the Related Art

There are methods and systems, which are well known in the art, for viewing internal portions of an object by directing radiation signals, generally referred to in the art as x-rays, onto the object and by receiving the radiation signals which pass through the object onto a recording medium, typically film. Ideally, the radiation signals will pass from the radiation source to the film in a straight line. However, as the radiation signals pass through the object, some of the signals are scattered so that they no longer travel in a straight line, which scattering causes reduced image quality. To reduce this effect, radiographic grids are placed between the object and film. Radiation grids are lead foil strips placed in a spaced apart relationship with each other, which spaced apart relationship is typically maintained by placing aluminum between the strips. The strips and aluminum are then packaged in a suitable covering. These grids, though effective for reducing radiation scattering, occasionally introduce artifacts such as grid lines into the image.

The film containing the captured image is processed in a variety of well known and utilized techniques for permitting on observer to view the image captured on the film. One such technique is to convert the image into a digitized form for displaying the image on a computer display and similar devices.

To convert the image into digitized form, typically, a digitizer converts the film into digital form for permitting the image to be displayed on a computer display by well known techniques.

Before displaying the image on the computer screen, grids lines, if there are any, should be removed. There are two well known methods in the art for reducing the effects of grid lines. One method utilizes moving the grids when the object of interest is radiated. The other method is to apply a processing algorithm to the computer system which is displaying the image.

Although the above methods for reducing grid lines are satisfactory, they are not without drawbacks. Moving grids involve a costly procedure and, in addition, require the object to be exposed to the radiation for a longer period of time than is normally required. This obviously is a drawback if the object is a person. For these reasons, they are not a preferred method of reducing the effects of grid lines. The processing algorithm is also costly and, as a secondary effect, can reduce the quality of the image.

Consequently, a need exists for a method of detecting grids so that costly processing algorithms for removing grids are applied only when there are grids in the image.

SUMMARY OF THE INVENTION

It is an object of the present invention to provide a method and system for detecting grids.

It is an advantage of the present invention to provide such a grid detection method and system which are cost effective and involve a minimum of time to implement.

It is a feature of the present invention to implement a high pass filter for removing the capture image from the digitized representation and to apply a statistical operation on the results for detecting the presence of grids.

The above and other objects, features and advantages of the present invention will become more apparent when taken in conjunction with the following description and drawings wherein like characters indicate like parts and which drawings form a part of the present invention.

With this object in view, the present invention resides in a method for detecting grids in a digital image having a plurality of pixels for capturing an image, comprising the steps of (a) performing a high pass filter operation on a sample of pixels for filtering out the image from the sampled pixels; and (b) performing a predetermined mathematical operation on the results of the high pass filter operation for determining when the digital image contains grids.

BRIEF DESCRIPTION OF THE DRAWINGS

In the course of the following detailed description, reference will be made to the attached drawings in which:

FIG. 4 is a plot in which FIG. 3 is smoothed; and

DETAILED DESCRIPTION OF THE INVENTION

Figure 1:
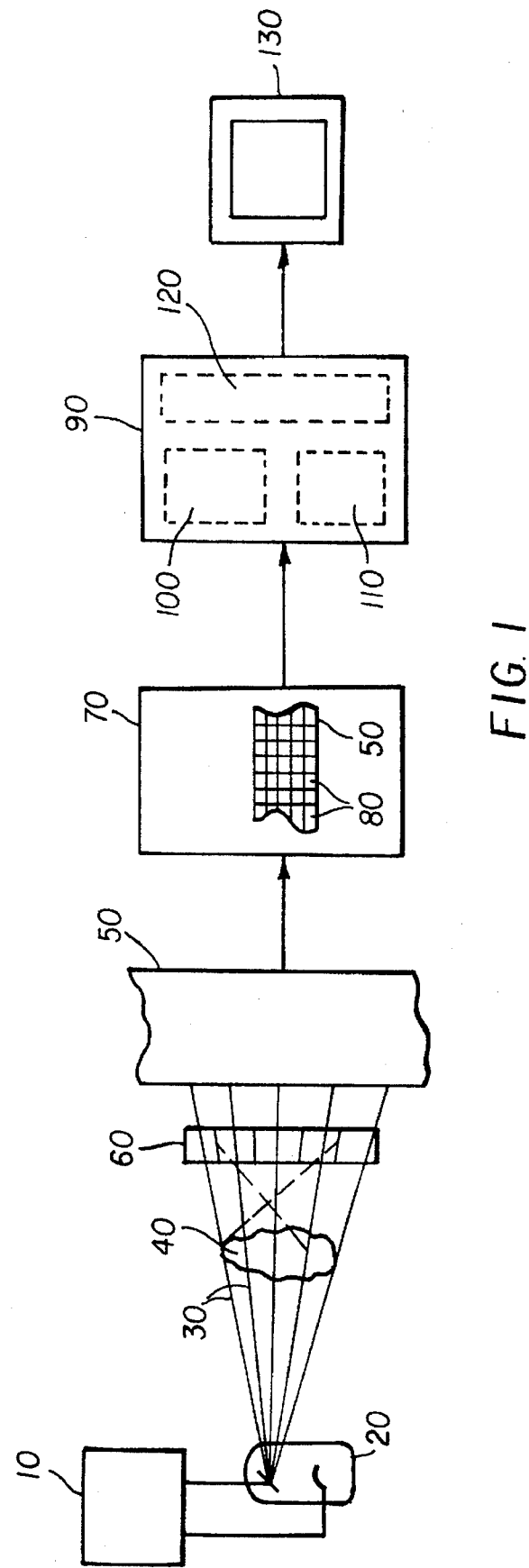
FIG. 1 is a drawing illustrating the environment of the present invention.

Referring to FIG. 1, there is illustrated a system for implementing the present invention. The system includes a high voltage generator 10 which powers an X-ray tube 20 for generating a beam of radiation signals 30, generally referred to as X-rays, for irradiating an object 40. The radiation signals pass through the object and are detected by a recording medium, typically film 50. As is illustrated by the dashed lines, some of the radiation signals are scattered as they pass through the object 40. These scattered signals reduce the image quality, and as a result, a well known and utilized radiographic grid 60 is placed between the object 40 and film 50 for reducing the effects of scattering.

The film 50, which now contains the captured image, is placed in a digitizer 70 for converting it into a digital format. During this conversion, the digitizer 70 scans one portion of the film 50, generally referred to in the art as a pixel 80, and assigns a pixel value to the pixel 80, which value represents the contents on the film 50 at that particular pixel 80. The digitizer 70 scans the entire image in the above described manner for converting each portion of the film 50, or pixel 80, into a pixel value. In essence, the digitized data represents each pixel 80 location and its corresponding pixel value. The film 50 is typically scanned in such a manner that in pixel representation the image includes a plurality of contiguous pixels 80 having a checkered array configuration.

The digitized data is passed to an image processor 90 where the data is stored in pixel format in a first 100 or second memory 110. In other words, a pixel location and its associated pixel value are stored in either of the two memories 100 and 110. The image processor 90 also contains an arithmetic unit 120 for performing arithmetic functions and other typical software functions. The image processor 90 upon command from a user can display the image stored in the memories 100 and 110 on a computer display 130.

Figure 2:
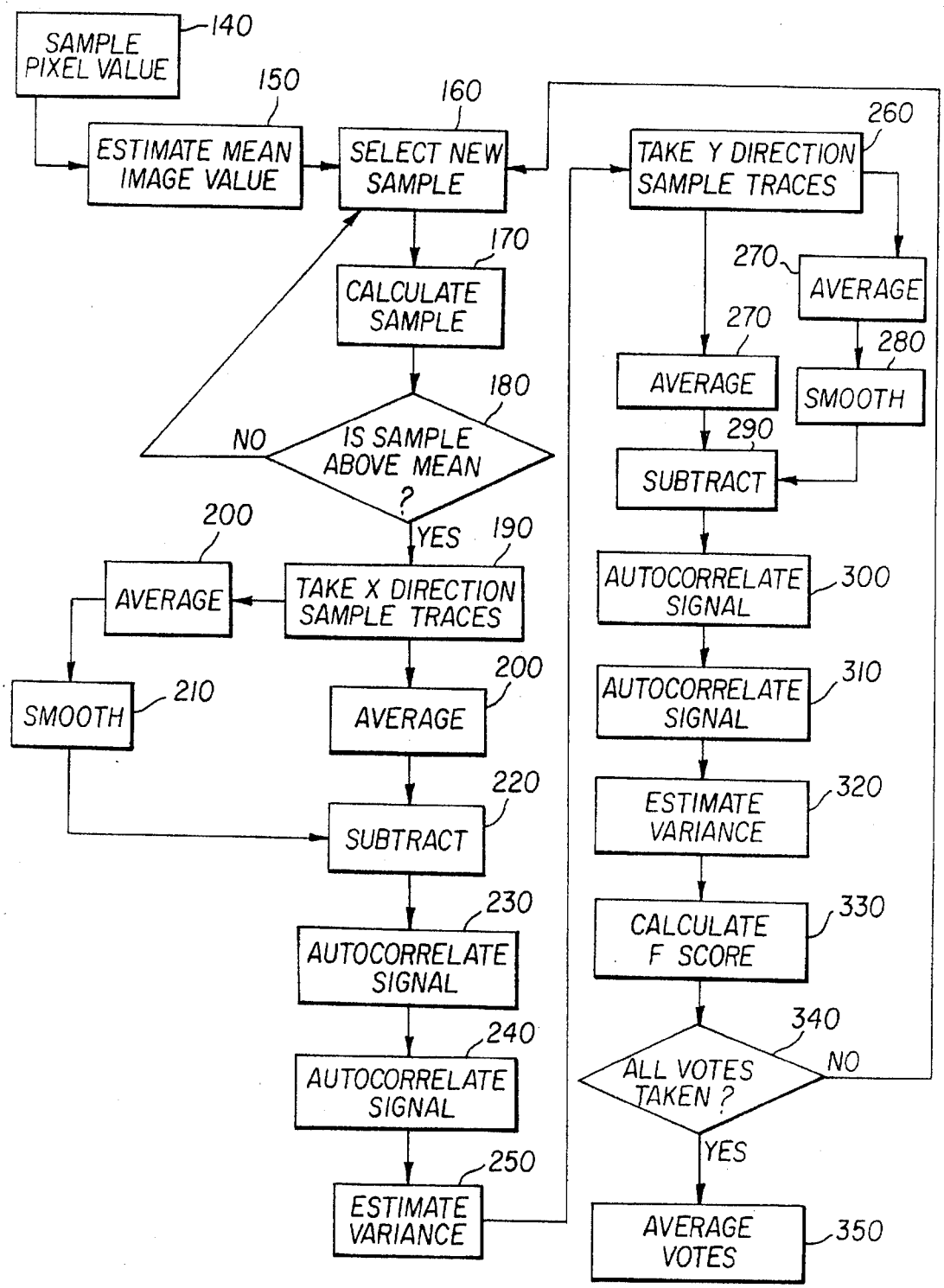
FIG. 2 is a flowchart of the method in accordance with the present invention.

However, before the image is displayed on the screen 130, a method of the present invention analyzes the image for the presence of grids which may have been created by the radiographic grids 60. Referring to FIG. 2, the method is illustrated in flowchart form. The image processor 90 loads a software program of the present invention which randomly samples 140 two percent of the pixel values stored in memory 100 and 110 for determining the mean value 150 of the sampled pixels 80, which mean value is an estimate of the mean of the entire image. It is instructive to note that two percent sampling is merely the percentage of the preferred embodiment and that any percentage of the pixels 80 may, in fact, be sampled for this estimation. Pixels 80 with a value of the mean or higher are an estimation of where it is easier to detect grids. Next, an array of pixels 80, preferably a 16×16 array, having a pixel value of the mean or higher is selected 160 for determining the mean value 170 of the 16×16 array. Again, although a 16×16 array is preferred, any size array may be used for this sample. If the array mean is below the estimated mean of the image 180, the array is discarded and another 16×16 array is sampled 160. If the array mean is at or above the estimated mean of the entire image 180, the array will be further analyzed for the presence of grids.

Figure 3:
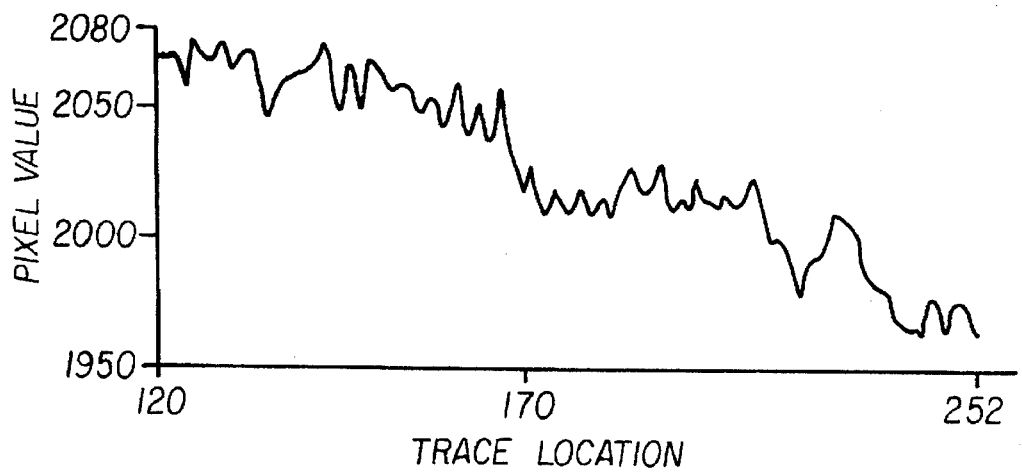
FIG. 3 is an example of a plot pixel value versus pixel location.
Figure 4:
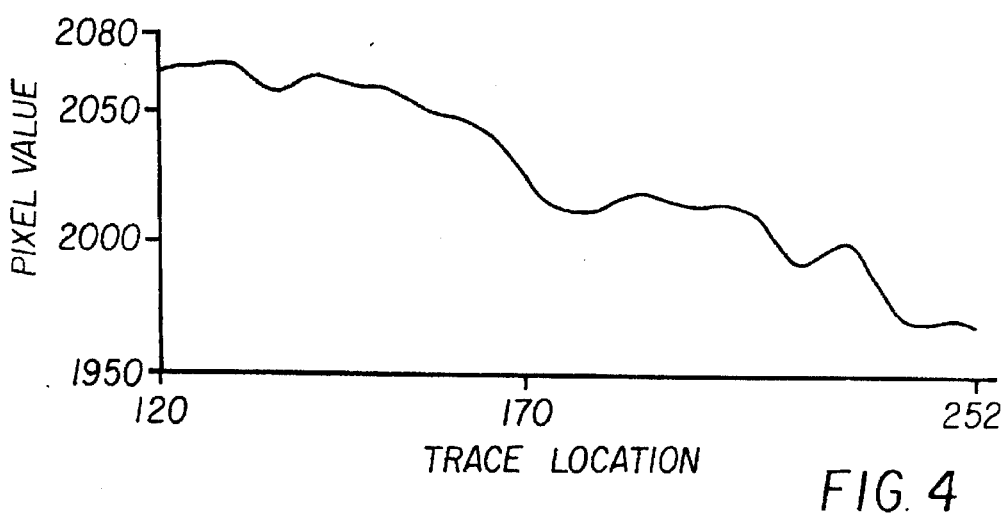
Figure 5:
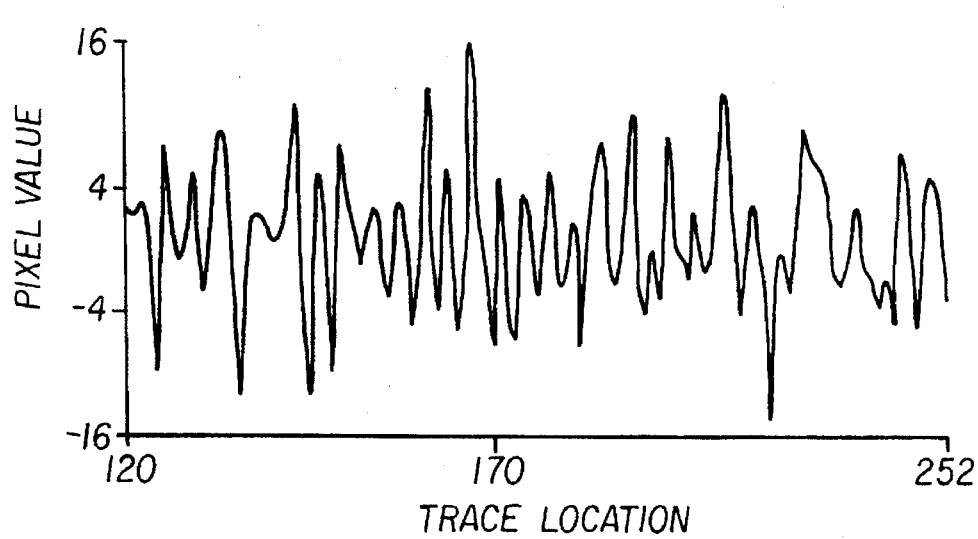
FIG. 5 is the subtraction of FIG. 4 from FIG. 3, a high pass filter.

The 16×16 array is further sampled by sampling two or more lines of pixels which are parallel to an imaginary x-axis or ordinate 190 which is through the center of the array. Each pixel 80 from each of the sampled lines which have a same ordinate is then averaged 200 together so that the result is an average pixel value along the ordinate. This result is plotted as a graph of pixel value versus pixel location along the ordinate. An example of such a plot is shown in FIG. 3. Referring back to the flowchart, this plot is smoothed 210 which is well known in the art and an illustration of which is shown in FIG. 4. (See Digital Picture Processing Picture, Rosenfeld and Kak, Academic Press 1982 for further disclosure of smoothing) The smoothed plot is subtracted 220 from the averaged plot for forming a high pass filter of the resultant pixels. An example of a plot of the high pass filter is shown in FIG. 5.

Referring to FIG. 2, the resultant high pass plot is autocorrelated 230 by techniques which are well known in the art for enhancing the high pass plot (See Detection of Signals in Noise, Whalen 1971 for further disclosure of autocorrelation). For further enhancement, the autocorrelated 240 plot is again autocorrelated for further still better quality. The variance, which is a well known statistical technique, is then calculated 230 from the result of this autocorrelation (See Probability and Statistics, DeGroet Addison Wesley 1975 for details of variance calculation).

Steps 190 through 250 are then repeated for sampling along the y-axis or abscissa, and are recited below for thoroughness of understanding. For example, the 16×16 array further samples two or lines of pixels which are parallel to an imaginary the abscissa 260 which is also through the center of the array. Each pixel from each of the sampled lines which have a same abscissa is then averaged 270 together so that the result is an average pixel value along the abscissa. This result is plotted as a graph of pixel value versus pixel location along the abscissa and the plot is smoothed 280. The smoothed plot is subtracted 290 from the averaged plot for forming a high pass filter of the resultant pixels.

The resultant high pass plot is autocorrelated 300 for enhancing the high pass plot. For further enhancement, the autocorrelated plot is again autocorrelated 310 for further still better quality. The variance is then calculated 320 from the result of this autocorrelation.

After the variances in both directions are calculated, a F-test 330 is used for determining whether grids are present in the 16×16 sampled array of pixels. The F-test is calculated as follows:

$$F = \frac{\sigma^2 \text{ Horizontal}}{\sigma^2 \text{ Vertical}} \quad \text{Equation (1)}$$

If the F-test score is greater than 1, this results in a determination that vertical grids are present in the sampled array, and a vote of positive one is given. If the F-test score is less than 1, this results in a determination that horizontal grids are present in the sampled array, and a vote of negative one is given. A F-test score of zero means that neither vertical nor horizontal grids are present, and a vote of zero is given.

If all of a predetermined percentage of pixels 80 with a mean value at or greater than the mean pixel value of the entire image have been included in a 16×16 array for analysis 340, the average of all the votes 350 are taken and the result indicates whether any grids are present and, if so, what direction they rest. The result of the average has the same meaning as the F-test score: positive one means vertical grids, negative one means horizontal grids are present, and a zero indicates no grids are present- If all the pixels have not been included in a 16×16 array for analysis 340, the above steps are repeated until they have been included in a 16×16 array analysis.

Referring back to FIG. 1, if a grid is present in the image, the image processor 90 applies a filter to the image for removing them. Such filters are well known in the art.

While there has been shown what is considered to be the preferred embodiment of the invention, it will be manifest that many changes and modifications may be made therein without departing from the essential spirit of the invention. It is intended, therefore, in the annexed claims, to cover all such changes and modifications as may fall within the true scope of the invention.

Parts List:

- 10 generator
- 20 x-ray tube
- 30 radiation signals
- 40 object
- 50 film
- 60 radiographic grid
- 70 digitizer
- 80 pixel
- 90 image processor
- 100 first memory
- 110 second memory
- 120 arithmetic unit
- 130 computer display
- 140 sampling real value step
- 150 estimating mean image value step
- 160 selecting new samples step
- 170 calculating mean step
- 180 sampling mean step
- 190 sampling trace step
- 200 averaging step
- 210 smoothing step
- 220 subtracting step
- 230 autocorrelating signal step 240 autocorrelating signal step
250 estimating variance step
260 sampling trace step
270 averaging step
280 smoothing step
290 subtracting step
300 autocorrelating signal step
310 autocorrelating signal step
320 estimating variance step
330 calculating F score step
340 voting step
350 averaging step

What is claimed is:

1. A method for detecting grids in a digital image having a plurality of pixels for capturing an image, comprising the steps of:
   (a) performing a high pass filter operation on a sample of pixels for filtering out the image from the sampled pixels; and
   (b) performing a F test operation on the results of the high pass filter operation for determining when the digital image contains grids; wherein the F test is F=horizontal variance/vertical variance and vertical grid lines are present when the F-test results in the F-test having the horizontal variance less than the vertical variance, and the horizontal grid lines are present when the horizontal variance is greater than the vertical variance.

2. The method as in claim 1 wherein the high pass filter operation includes the steps of:
   (a1) forming a plot of pixel location versus the pixel value at the corresponding pixel location;
   (a2) smoothing the results of the plotting operation; and
   (a3) subtracting each plotted pixel value and each smoothed pixel value which are from the same pixel location for obtaining the high pass filter.

3. The method as in claim 2 wherein step (a1) includes:
   (ai) further sampling from the sampled pixels at least two spaced apart lines of pixels;
   (aii) averaging pixel values from each of the spaced apart lines which have a matching abscissa for removing noise from the digital image; and
   (aiii) forming the plot in step (a1) from the averaged pixel values.

4. The method as in claim 3 wherein step (aii) includes averaging pixel values from each of the spaced apart lines which have a matching ordinate for removing noise from the digital image.

5. The method as in claim 4 wherein the plot is autocorrelated for enhancing the plot.

6. The method as in claim 1 wherein no grids are present in the digital image when either of the conditions in step (b) are not met.

7. The method as in claim 6 wherein each of the sampled pixels designate a first signal if vertical grids are detected and designate a second signal if horizontal grids are detected for determining which of the first or second signals have a majority which, in turn, determines whether the digital image has vertical or horizontal signals.

8. A method for detecting grids in a digital image having a plurality of pixels for capturing an image, comprising the steps of:
   (a) determining a pixel value for selecting which pixels in the digital image meet a predetermined test which is defined by the predetermined pixel value;
   (b) performing a high pass filter operation on a sample of pixels containing at least one of the pixels which meets the predetermined test for filtering out the image from the sampled pixels; and
   (c) performing a F-test operation on the results of the high pass filter operation for determining when the image contains grids; wherein the F test is F=horizontal variance/vertical variance and vertical grid lines are present when the F-test results in the F-test having the horizontal variance less than the vertical variance, and the horizontal grid lines are present when the horizontal variance is greater than the vertical variance.

9. The method as in claim 8 wherein the high pass filter operation includes the steps of:
   (a1) forming a plot of pixel location versus the pixel value at the corresponding pixel location;
   (a2) smoothing the results of the plotting operation; and
   (a3) subtracting each plotted pixel value and each smoothed pixel value which are from the same pixel location for obtaining the high pass filter.

10. The method as in claim 9 wherein step (a1) includes:
    (ai) further sampling from the sampled pixels at least two spaced apart lines of pixels;
    (aii) averaging pixel values from each of the spaced apart lines which have a matching abscissa for removing noise from the digital image; and
    (aiii) forming the plot in step (a1) from the averaged pixel values.

11. The method as in claim 10 wherein step (aii) includes averaging pixel values from each of the spaced apart lines which have a matching ordinate for removing noise from the digital image.

12. The method as in claim 8 wherein the predetermined test is determining the mean of the pixel values.

13. The method as in claim 12 wherein the high pass filter operation is performed on the sample containing at least one of the pixel values at or higher than the mean pixel value.

14. A system for detecting grids in a digital image having a polarity of pixels for capturing an image, comprising:
    (a) means for high pass filtering a sample of pixels for filtering out the image from the sampled pixels; and
    (b) means for performing a F-test operation on the results of said high pass filter means for determining when the digital image contains grids; wherein the F test is F=horizontal variance/vertical variance and vertical grid lines are present when the F-test results in the F-test having the horizontal variance less than the vertical variance, and the horizontal grid lines are present when the horizontal variance is greater than the vertical variance.

15. The system as in claim 14 wherein the predetermined mathematical operation includes a F-test.

16. The system as in claim 14 wherein said high pass filter includes:
    (a1) means for plotting pixel location versus the pixel value at the corresponding pixel location;
    (a2) means for smoothing the results of the plotting operation; and
    (a3) means for subtracting each plotted pixel value and each smoothed pixel value which are from the same pixel location for obtaining the high pass filter.

17. The system as in claim 16 wherein said plotting means includes:
    (ai) means for sampling from the sampled pixels at least two spaced apart lines of pixels;

(aii) means for averaging pixel values from each of the spaced apart lines which have a matching abscissa for removing noise from the digital image; and (aiii) means for forming the plot from the averaged pixel values.

18. The system as in claim 17 wherein said averaging means includes averaging pixel values from each of the spaced apart lines which have a matching ordinate for removing noise from the digital image.

* * * * *